United States Patent [19]
Rose et al.

[11] Patent Number: 5,827,649
[45] Date of Patent: Oct. 27, 1998

[54] KITS FOR NUCLEIC ACID AMPLIFICATION KIT USING SINGLE PRIMER

[75] Inventors: Samuel Rose; Thomas C. Goodman; Linda M. Western, all of Mountain View; Martin Becker, Palo Alto; Edwin F. Ullman, Atherton, all of Calif.

[73] Assignee: Behring Diagnostics GmbH, Deerfield, Ill.

[21] Appl. No.: 242,931

[22] Filed: May 16, 1994

Related U.S. Application Data

[63] Continuation of Ser. No. 109,852, Aug. 20, 1993, abandoned, which is a continuation of Ser. No. 734,030, Jul. 22, 1991, abandoned, which is a continuation of Ser. No. 399,795, Aug. 29, 1989, abandoned, which is a continuation-in-part of Ser. No. 299,282, Jan. 19, 1989, abandoned.

[51] Int. Cl.$^6$ ........................................... C12Q 1/68
[52] U.S. Cl. ............................. 435/6; 435/91.1; 435/91.2; 536/23.1; 536/24.1; 536/24.3; 536/24.31; 536/24.32; 536/24.33; 935/77; 935/78
[58] Field of Search .................................. 435/5, 6, 91.1, 435/91.2; 536/23.1, 24.1, 24.3–24.33; 935/77, 78, 88

[56] References Cited

U.S. PATENT DOCUMENTS 5,185,243   2/1993   Ullman et al. .............................. 435/6

*Primary Examiner*—Ardin H. Marschel
*Attorney, Agent, or Firm*—Theodore J. Leitereg

[57] ABSTRACT

A method is disclosed for determining the presence of a polynucleotide analyte in a sample suspected of containing the analyte. The method comprises (a) forming as a result of the presence of an analyte a single stranded polynucleotide comprising a target polynucleotide binding sequence flanked by first and second polynucleotide sequences that differ from the sequence of the analyte or a sequence complementary to the analyte sequence, (b) forming multiple copies of the single stranded polynucleotide, and (c) detecting the single stranded polynucleotide. Also disclosed is a method of producing at least one copy of a single stranded polynucleotide. The method comprises (a) forming in the presence of nucleoside triphosphates and template dependent polynucleotide polymerase an extension of a polynucleotide primer at least the 3'-end of which has at least a 10 base sequence hybridizable with a second sequence flanking the 3'-end of the single stranded polynucleotide, the second sequence being partially or fully complementary with at least a 10 base first sequence flanking the 5' end of the single stranded polynucleotide, (b) dissociating the extended polynucleotide primer and the single stranded polynucleotide, (c) repeating step a and (d) dissociating the extended polynucleotide primer and the copy of the single stranded polynucleotide.

5 Claims, 5 Drawing Sheets

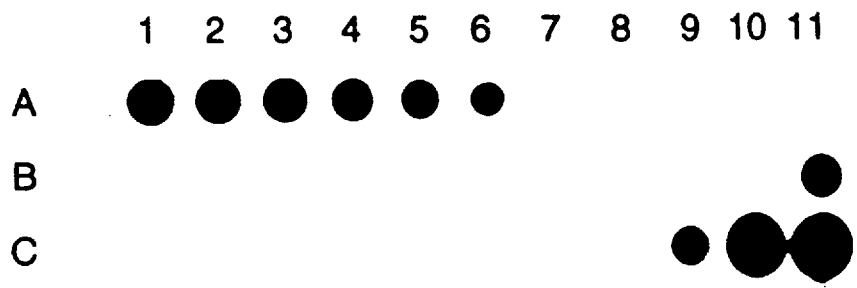
FIG._1
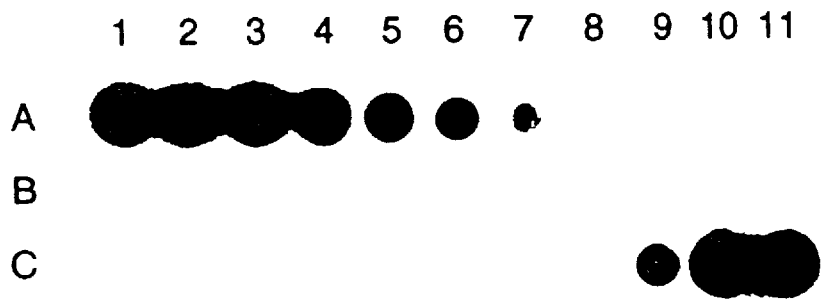
FIG._2
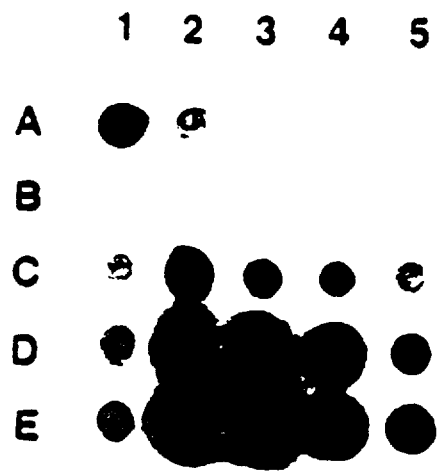
FIG._3

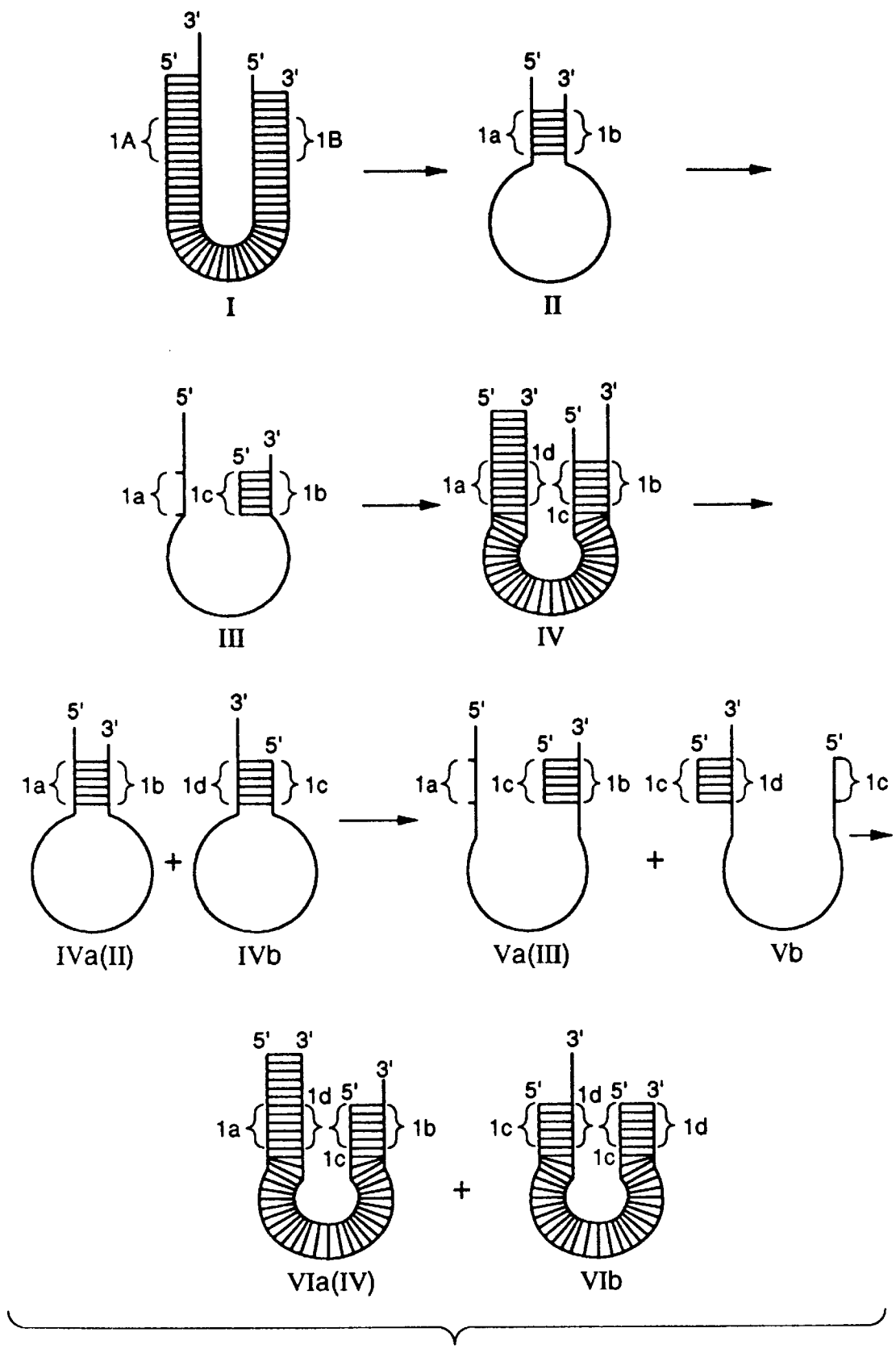
FIG._4

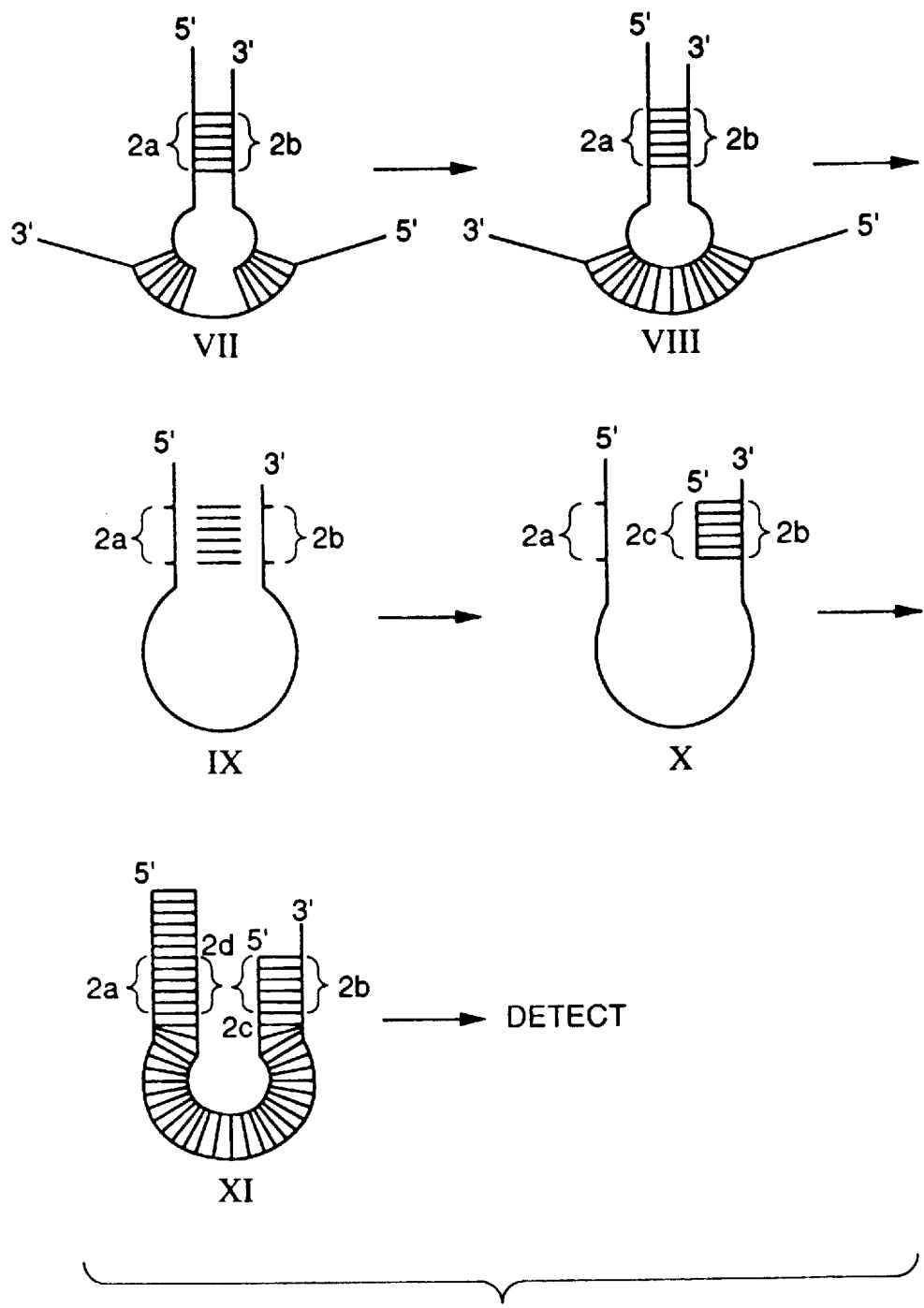
FIG._5

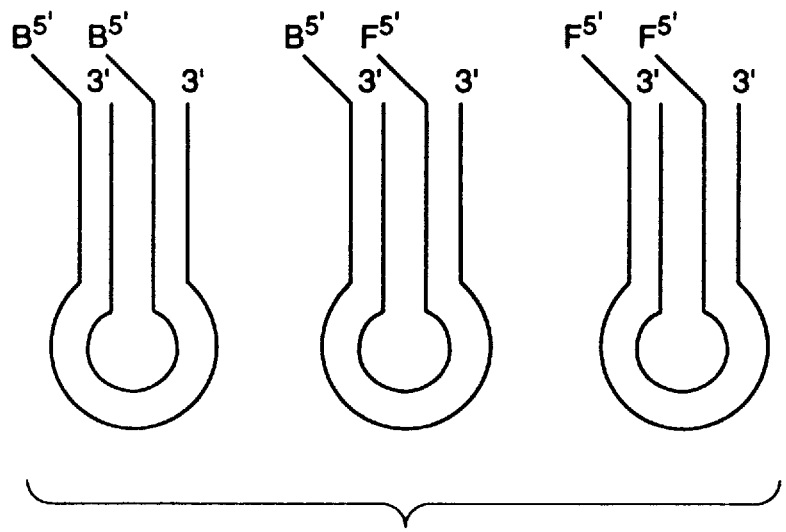
FIG._6
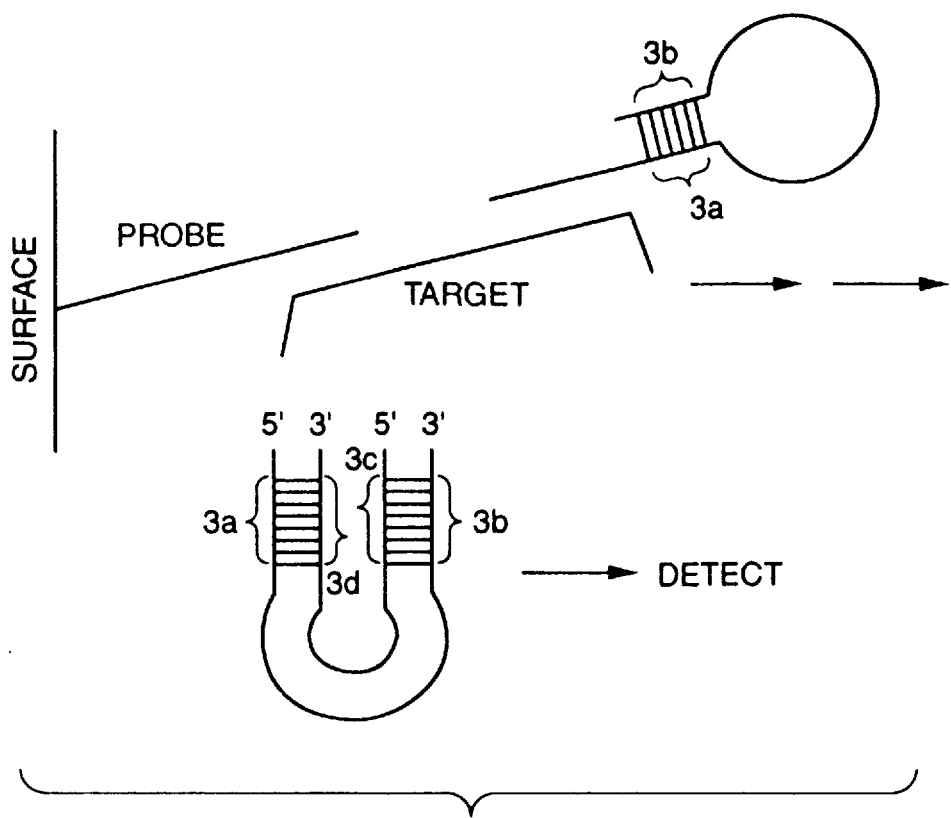
FIG._7

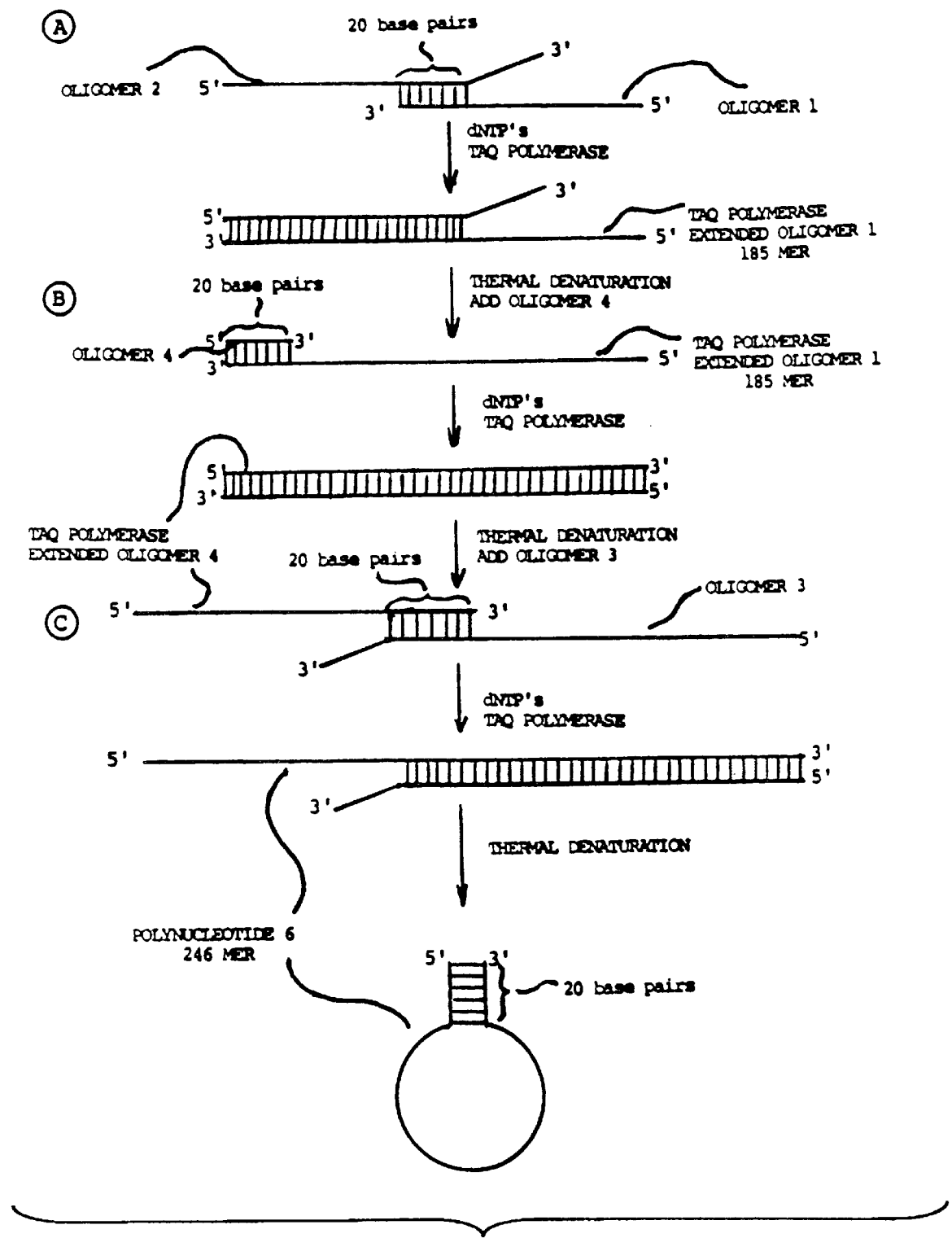
FIG._8

KITS FOR NUCLEIC ACID AMPLIFICATION KIT USING SINGLE PRIMER

This is a Continuation of application Ser. No. 08/109,852, filed Aug. 20, 1993 now abandoned, which in turn is a file wrapper continuation of Ser. No. 07/734,030, filed Jul. 22, 1991 now abandoned, which in turn is a file wrapper continuation of application Ser. No. 07/399,795, filed Aug. 29, 1989 now abandoned, which in turn is a continuation-in-part of application Ser. No. 07/299,282, filed Jan. 19, 1989 now abandoned, the disclosures of which are incorporated herein by reference.

BACKGROUND OF THE INVENTION

1. Field of the Invention.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

2. Description of the Prior Art.

A process for amplifying, detecting and/or cloning nucleic acid sequences is disclosed in U.S. Pat. Nos. 4,683,195 and 4,683,202. Sequence polymerization by polymerase chain reaction is described by Saiki, et al., (1986) Science, 230: 1350–1354. A method of making an oligonucleotide is described in European Patent Application No. 0194545 A2. Belgian Patent Application No. BE 904402 discloses a mold for making DNA detection probes. Gene amplification in eukaryotic cells is disclosed in U.S. Pat. No. 4,656,134.

Langer, et al., Proc, Natl. Acad. Sci. USA, (1981) 78: 6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., Virology, (1983) 126: 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European Patent Application 83106112.2 (Priority U.S. patent application Ser. No. 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European Patent Application No. 0164054 A1. U.S. Pat. No. 4,663,283 describes a method of altering double-stranded DNA.

Genomic amplification with transcript sequencing is discussed by Stoflet, et al., Science (198) 239:491. Primer-directed enzymatic amplification of DNA with a thermostable DNA polymerase is described by Saiki, et al., Science (1988) 239:487. U.S. Pat. No. 4,724,202 discloses the use of non-hybridizable nucleic acids for the detection of nucleic acid hybridization. Bugawan, et al., describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. A single stranded self-hybridizing nucleic acid probe capable of repeatedly hybridizing to itself or other nucleic acids to form an amplified entity is described in U.S. patent application Ser. No. 888,058, filed Jul. 22, 1986. U.S. Pat. Nos. 4,683,195 and 4,683,202 disclose a homogeneous polynucleotide displacement assay with digestion of the displaced RNA single strand polynucleotide from the reagent complex and amplifying nucleic acid sequences with treatment of separate complementary strands of the nucleic acid with two oligonucleotide primers. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14: 9171–9191. Cleavage of single stranded oligonucleotides by Eco RI restriction endonuclease is described in *Nucleic Acid Research* (1987) 15: 709–716.

Exponential Amplification of Recombinant-RNA Hybridization Probes is described by Lizardi, et al. (1988) *Bio/Technology* 6:1197–1202. Fahrlander, et al., discusses Amplifying DNA Probe Signals: A Christmas Tree Approach in *Bio/Technology* (1988) 6:1165–1168.

A nucleic acid hybridization assay employing probes cross-linkable to target sequences is described in U.S. Pat. No. 4,599,303. The method involves the preparation of a specific single stranded ribonucleic acid or deoxyribonucleic acid molecule into which a bifunctional cross-linking molecule has been covalently incorporated. The incorporation is such that the cross-linking molecule retains the capacity to undergo a second reaction with the nucleic acid of the bacterial, viral, or mammalian chromosome, which is the target for the probe such as to form a covalent cross link. Following cross-linking, the uncrossed link probe is separated from covalently cross-linked probe-target complex using one of several procedures which differentiate between single stranded probe and double stranded covalently linked probe-target complex.

Detection of target sequences in nucleic acids by hybridization using diagnostic and contiguous probes for diagnosis of genetic abnormality diseases, especially in an automated procedure, is described in European Patent Application No. 0 185 494A2. In the method a sample is hybridized with a probe complementary to a diagnostic portion of the target sequence (the diagnostic probe) and with a probe complementary to a nucleotide sequence contiguous with the diagnostic portion (the contiguous probe) under conditions wherein the diagnostic probe remains bound substantially only to the sample nucleic acid containing the target sequence. The diagnostic probe and contiguous probe are then covalently attached to yield a target probe that is complementary to the target sequence and the probes which are not attached are removed. In a preferred mode, one of the probes is labeled so that the presence or absence of the target sequence can then be tested by melting the sample nucleic acid target probe duplex, eluting the dissociated target probe, and testing for the label.

The above method suffers at least one disadvantage in that contiguous sequences are required. To carry out the method, one must identify the diagnostic sequence and the contiguous sequence and create diagnostic and contiguous probes complementary to the above sequences. If the diagnostic and contiguous sequences are not identified precisely, then the diagnostic and contiguous probes may not hybridize sufficiently and the assay specificity and sensitivity can be lost or substantially decreased.

SUMMARY OF THE INVENTION

The invention disclosed herein includes methods and reagents for producing multiple copies of a single stranded polynucleotide wherein a single polynucleotide primer is employed. As a result, the number of reagents and assay steps is decreased over known methods.

In one embodiment of the invention, at least one copy of a single stranded polynucleotide is produced by a method which comprises: (a) forming in the presence of nucleoside triphosphates and template dependent polynucleotide polymerase along the single stranded polynucleotide an extension of a polynucleotide primer at least the 3'-end of which has at least a 10 base sequence hybridizable with a second flanking sequence at the 3'-end of the single stranded polynucleotide, the second flanking sequence being partially or fully complementary with at least a 10 base first flanking sequence at the 5'-end of the single stranded polynucleotide, (b) dissociating the extended polynucleotide primer and the single stranded polynucleotide, and (c) repeating step (a).

Another aspect of the invention involves a method of producing multiple copies of a polynucleotide sequence. The method comprises providing in combination (1) a single stranded polynucleotide having the polynucleotide sequence and being flanked at each end by partially or fully complementary first and second flanking sequences, (2) a polynucleotide primer at least a 10 base portion of which at its 3'-end is hybridizable to that member of the first and second flanking sequences that is at the 3'-end of the single stranded polynucleotide, (3) nucleoside triphosphates, and (4) template dependent polynucleotide polymerase. The combination is incubated under conditions for either wholly or partially sequentially or concomitantly (1) dissociating the single stranded polynucleotide from any complementary sequence with which it is hybridized, (2) hybridizing the polynucleotide primer with the flanking sequence at the 3'-end of the single stranded polynucleotide, (3) extending the polynucleotide primer along the single stranded polynucleotide to provide a first extended polynucleotide primer, (4) dissociating the first extended polynucleotide primer and the single stranded polynucleotide, (5) hybridizing the first extended polynucleotide primer with the polynucleotide primer, (6) extending the polynucleotide primer along the first extended polynucleotide primer to provide a second extended polynucleotide primer, (7) dissociating the second extended polynucleotide primer from the first extended polynucleotide primer, and (8) repeating steps (5)–(7).

Another embodiment concerns a method of producing multiple copies of a polynucleotide sequence in a polynucleotide wherein the sequence is flanked at each end by a different member of a pair of flanking sequences that are partially or fully complementary to each other. The method comprises (a) combining the polynucleotide with a single polynucleotide primer having at least a terminal sequence at its 3'-end at least partially complementary to and hybridizable with at least a portion of the member of the pair of flanking sequences at the 3'-end of the polynucleotide sequence, nucleoside triphosphates, and template dependent polynucleotide polymerase. The combination is incubated under conditions for either wholly or partially sequentially or concomitantly (1) dissociating the polynucleotide sequence from any sequence with which it is hybridized to provide a single stranded polynucleotide, (2) hybridizing the polynucleotide primer with the flanking sequence at the 3'-end of the single stranded polynucleotide, (3) extending the polynucleotide primer along the single stranded polynucleotide to provide an extended polynucleotide primer (4) dissociating the first extended polynucleotide primer and the single stranded polynucleotide, (5) hybridizing the first extended polynucleotide primer with the polynucleotide primer, (6) extending the polynucleotide primer along the first extended polynucleotide primer to provide a second extended polynucleotide primer, (7) dissociating the second extended primer from the first extended polynucleotide primer, and (8) repeating steps (5)–(7) above.

The above methods have application in facilitating the determination of the presence of a polynucleotide analyte in a sample suspected of containing such polynucleotide analyte. The target polynucleotide sequence can be DNA or RNA.

In one embodiment of this aspect of the invention the method comprises (a) forming as a result of the presence of an analyte a single stranded polynucleotide flanked by complementary first and second flanking sequences, (b) forming multiple copies of the single stranded polynucleotide and the flanking sequences, and (c) detecting the single stranded polynucleotide. Any method for detecting specific nucleic acids or polynucleotides can be used. Multiple copies of the single stranded polynucleotide can be made by, for example, any of the aforementioned methods.

In one particular method for determining the presence of a polynucleotide analyte in a sample suspected of containing the analyte, a single stranded polynucleotide flanked by at least 80% complementary first and second flanking sequences, each comprised of at least 15 bases, is formed as a result of the presence of the analyte. In the presence of nucleoside triphosphates and template dependent polynucleotide polymerase an extension is formed of a polynucleotide primer at least the 3'-end of which can hybridize with the second sequence at the 3'-end of the single stranded polynucleotide. Extended polynucleotide primer containing a sequence identical to and/or complementary with the single stranded polynucleotide is then detected, the presence thereof indicating the presence of the polynucleotide analyte.

Another aspect of the present invention concerns an analytical method which comprises contacting a sample suspected of containing the analyte with first and second polynucleotide probes. The first probe comprises a sequence at its 3'-end complementary to a first portion of one strand of the analyte and a first flanking sequence. The second probe comprises a sequence at its 5'-end complementary to a second portion of the same strand of the analyte and a second flanking sequence. The first and second flanking sequences are partially or fully complementary. The contact is carried out under conditions for binding of the first and second probes with the analyte. Conditions are provided for ligating the first and second polynucleotide probes to one another only when bound to the analyte. An extension of a polynucleotide primer at least the 3'-end of which can hybridize with the flanking sequence is formed in the presence of nucleoside triphosphates and template dependent polynucleotide polymerase. Extended polynucleotide primer containing a sequence complementary to the first probe is detected, the presence thereof indicating the presence of the analyte. Another aspect of the present invention involves a method for detecting the presence of a polynucleotide analyte in a sample suspected of containing the analyte. The method comprises the steps of (a) ligating third and fourth sequences of a polynucleotide probe, the third sequence having a free 3'-end and the fourth sequence having a free 5'-end and each being hybridizable to separate portions of the analyte and ligatable, or capable of being rendered ligatable, only in the presence of the analyte, the polynucleotide probe further comprising first and second flanking sequences, wherein the first sequence is 5' of the third sequence, the second sequence is 5' of the first sequence and the fourth sequence is 5' of the second sequence, (b) forming in the presence of nucleoside triphosphates and template dependent polynucleotide polymerase an extension of a polynucleotide primer at least the 3'-end of which can hybridize with the second flanking sequence of the polynucleotide probe, and detecting extended polynucleotide primer containing a sequence identical to and/or complementary with at least that portion of the ligated third or fourth sequences complementary to the separate portions of the analyte.

Another analytical method in accordance with the present invention comprises contacting a sample suspected of containing an analyte with first and second polynucleotide probes. The first probe comprises (1) a first flanking sequence partially or fully complementary to a second flanking sequence in the second probe and (2) a sequence complementary to a portion of the analyte other than a portion partially or fully complementary to the second probe. The first and second probes are ligatable, or capable of being rendered ligatable, to one another only when bound to the analyte. The method further comprises forming in the presence of nucleoside triphosphates and template dependent polynucleotide polymerase an extension of a polynucleotide primer at least a portion of which can be hybridized with the flanking sequence of that probe which is ligated to the 3'-end of the other probe. Extended polynucleotide primer and/or ligated first and second polynucleotide probes are then detected.

BRIEF DESCRIPTION OF THE DRAWINGS

FIG. 1 is a dot-blot hybridization of $^{32}$P oligomer 5 to single primer polynucleotide amplification products.

FIG. 2 is a dot-blot hybridization of a $^{32}$P oligomer 9 to single primer polynucleotide amplification products.

FIG. 3 is a dot-blot hybridization of $^{32}$P oligomer 5 to single primer polynucleotide amplification products.

FIG. 4 is a schematic representation of one embodiment of the present invention.

FIG. 5 is an example of the determination of a polynucleotide analyte in accordance with the present invention.

FIG. 6 is an alternate embodiment of the present invention utilizing certain labels.

FIG. 7 is an alternate embodiment of the present invention.

FIG. 8 is an schematic representation of a method for target dependent formation of hairpin molecule substrate capable of single primer amplification in accordance with the present invention.

DESCRIPTION OF THE SPECIFIC EMBODIMENTS

The present method allows the production of at least one copy and preferably multiple copies of a single stranded polynucleotide. The single stranded polynucleotide can be present in a medium or can be formed by the presence of a polynucleotide analyte in a sample suspected of containing the analyte. In the production of multiple copies of the single stranded polynucleotide the following components are provided: (i) the single stranded polynucleotide, (ii) a polynucleotide primer at least the 3'-end of which has at least a 10 base, preferably at least a 15 base sequence hybridizable with a second flanking sequence connected to the 3'-end of the single stranded polynucleotide, (iii) nucleoside triphosphates, and (iv) template-dependent polynucleotide polymerase. The second flanking sequence connected to the single stranded polynucleotide sequence is usually at least 65% complementary with at least a 10 base, preferably a 15 base, first flanking sequence connected to the 5'-end of the single stranded polynucleotide. After extension of the primer along the single stranded polynucleotide and the first flanking sequence, the extended polynucleotide sequence is dissociated from the single stranded polynucleotide. Extension and dissociation are repeated until a desired number of copies is obtained.

One aspect of the invention comprises a determination of a polynucleotide analyte by causing the formation of a single stranded polynucleotide and initiating the above described method for producing multiple copies. In this method the single stranded polynucleotide is flanked by first and second polynucleotide flanking sequences that differ from the sequence of the analyte or a sequence complementary to the analyte. The presence of the analyte is determined by detection a sequence located at or beyond the 3' end of the first flanking sequence linked to a sequence located at or beyond the 5' end of the second flanking sequence.

Before proceeding further with a description of the specific embodiments of the present invention, a number of terms will be defined.

Polynucleotide analyte—a compound or composition to be measured which is a polymeric nucleotide having about 20 to 500,000 or more nucleotides, usually about 100 to 200,000 nucleotides, more frequently 500 to 15,000 nucleotides. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: | |
|---|---|
| Corynebacteria | |
| Corynebacterium diphtheria | |
| Pneumococci | |
| Diplococcus pneumoniae | |
| Streptococci | |
| Streptococcus pyrogenes | |
| Streptococcus salivarus | |
| Staphylococci | |
| Staphylococcus aureus | |
| Staphylococcus albus | |
| Neisseria | |
| Neisseria meningitidis | |
| Neisseria gonorrhea | |
| Enterobacteriaciae | |
| Escherichia coli | |
| Aerobacter aerogenes | The colliform |
| Klebsiella pneumoniae | bacteria |
| Salmonella typhosa | |
| Salmonella choleraesuis | The Salmonellae |
| Salmonella typhimurium | |
| Shigella dysenteria | |
| Shigella schmitzii | |

TABLE I-continued

| Microorganisms of interest include: | |
|---|---|
| Shigella arabinotarda | |
| | The Shigellae |
| Shigella flexneri | |
| Shigella boydii | |
| Shigella sonnei | |
| Other enteric bacilli | |
| Proteus vulgaris | |
| Proteus mirabilis | Proteus species |
| Proteus morgani | |
| Pseudomonas aeruginosa | |
| Alcaligenes faecalis | |
| Vibrio cholerae | |
| Hemophilus-Bordetella group | Rhizopus oryzae |
| Hemophilus influenza, H. ducryi | Rhizopus Phycomycetes arrhizua |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| Pasteurella pestis | Cladosporium carrionii |
| Pasteurella tulareusis | Phialophora verrucosa |
| Brucellae | Aspergillus nidulans |
| Brucella melitensis | Madurella mycetomi |
| Brucella abortus | Madurella grisea |
| Brucella suis | Allescheria boydii |
| Aerobic Spore-forming Bacilli | Phialophora jeanselmei |
| Bacillus anthracis | Microsporum gypseum |
| Bacillus subtilis | Trichophyton mentagrophytes |
| Bacillus megaterium | Keratinomyces ajelloi |
| Bacillus cereus | Microsporum canis |
| Anaerobic Spore-forming Bacilli | Trichophyton rubrum |
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histolyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-like bacteria) | Picornaviruses |
| Actinomyces Isaeli | Poliovirus |
| Actinomyces bovis | Coxsackievirus |
| Actinomyces naeslundii | Echoviruses |
| Nocardia asteroides | Rhinoviruses |
| Nocardia brasiliensis | Myxoviruses |
| The Spirochetes | Influenza (A, B, and C) |
| Treponema pallidum  Spirillum minus | Parainfluenza (1–4) |
| Treponema pertenue  Streptobacilius monoiliformis | Mumps Virus Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| Trypanasomes | Rubella Virus |
| Mycoplasmas | Arboviruses |
| Mycopiasma pneumoniae | |

TABLE I-continued

Microorganisms of interest include:

| Other pathogens | Eastern Equine Eucephalitis Virus |
|---|---|
| Listeria monocytogenes | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites | Hepatitis B Virus |
| bacterial/viral) | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* | |
| (*Absidia corymbifera*) | |

The polynucleotide analyte, where appropriate, may be treated to cleave the analyte to obtain a fragment that contains a target polynucleotide sequence, for example, by shearing or by treatment with a restriction endonuclease or other site specific chemical cleavage method.

For purposes of this invention, the polynucleotide analyte, or the cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°–100° C. for a period of about 1 to 10 minutes to produce denatured material.

Target polynucleotide sequence—a sequence of nucleotides to be identified, the identity of which is known to an extent sufficient to allow preparation of polynucleotide probes that are complementary to and will hybridize with at least a portion of such target sequence. The target polynucleotide sequence usually will contain from about 12 to 1000 or more nucleotides, preferably 20 to 100 nucleotides. The target polynucleotide sequence is frequently a part of the polynucleotide analyte. The target polynucleotide sequence will generally be a fraction of a larger molecule or it may be substantially the entire molecule. The minimum number of nucleotides in the target polynucleotide sequence will be selected to assure that the presence of target polynucleotide sequence in a sample will be a specific indicator of the presence of polynucleotide analyte in a sample. Very roughly, the sequence length will usually be greater than about 1.6 log L nucleotides where L is the number of base pairs in the genome of the biologic source of the sample. The maximum number of nucleotides in the target sequence will normally be governed by the length of the polynucleotide analyte and its tendency to be broken by shearing, by endogenous nucleases or by reagents used to cleave the target sequence.

Single stranded polynucleotide—a natural or synthetic sequence of nucleotides that exists naturally or is preformed or is formed from a probe as the result of the presence of an analyte. It will normally be comprised at least of a sequence that is identical to or complementary with at least a portion of the target polynucleotide sequence and may also contain one or more sequences which, when bound to their complementary sequences, are specific binding sites for receptors such as repressors, restriction enzymes, and the like. The single stranded polynucleotide is flanked by a first flanking sequence and a second flanking sequence which have at least 50% complementary base sequences, usually at least 65% complementary base sequences, often at least 80% complementary base sequences. The first and second flanking sequences are attached to the 3'-end and 5'-end, respectively, of the single stranded polynucleotide and each comprises at least ten, preferably at least 15, nucleotides, deoxynucleotides, and/or derivatives thereof.

The single stranded polynucleotide together with the flanking sequences and polynucleotides attached thereto will usually contain from 30 to 3,000 nucleotides, preferably 50 to 500 nucleotides. The single stranded polynucleotide can be RNA or DNA and can also be a synthetic oligonucleotide. When the single stranded polynucleotide flanked by the first and second sequences is hybridized with a complementary strand, it will frequently form inverted repeats.

Polynucleotide primer—a polynucleotide containing a sequence at its 3'-end hybridizable with the second flanking sequence at the 3'-end of the single stranded polynucleotide. The number of nucleotides in the polynucleotide primer that are hybridizable with the second flanking sequence should be such that stringency conditions used to hybridize the polynucleotide primer will prevent excessive random non-specific hybridization. Usually, the number of nucleotides in the polynucleotide primer will be at least as great as in the second flanking sequence, namely, at least ten nucleotides, preferably at least 15 nucleotides and generally from about 10 to 2,000, preferably 20 to 100, nucleotides.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component Clq, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

The surface will usually be polyfunctional or be capable of being polyfunctionalized or be capable of binding an oligonucleotide or an sbp member through specific or nonspecific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cuatrecasas, *J. Biol. Chem.*, 245,3059 (1970). The length of a linking group to the oligonucleotide or sbp member may vary widely, depending upon the nature of the compound being linked, the effect of the distance between the compound being linked and the particle on the hybridization of the sequences and the like. The oligonucleotide or sbp member will be substantially bound to the outer surface of the particle.

Particles employed as the surface can be fluorescent either directly or by virtue of fluorescent compounds or fluorescers bound to the particle in conventional ways. The fluorescers will usually be dissolved in or bound covalently or non-covalently to the particle and will frequently be substantially uniformly bound through the particle. Fluoresceinated latex particles are taught in U.S. Pat. No. 3,853,987.

Label or reporter group—A member of the signal producing system that is conjugated to or becomes bound to a probe and is capable of being detected directly or, through a specific binding reaction, can produce a detectible signal. Labels include a polynucleotide primer or specific polynucleotide sequence that can provide a template for amplification or ligation or act as a ligand such as for a repressor protein. Preferably, one of the polynucleotide probes will have, or be capable of having, a label. In general, any label that is detectable can be used. The label can be isotopic or nonisotopic, usually non-isotopic, and can be a catalyst, dye, fluorescent molecule, chemiluminescer, coenzyme, enzyme, substrate, radioactive group, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of polynucleotide analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and β-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The organic particles will normally be comprised of polymers, either addition or condensation polymers, which are readily dispersible in the assay medium. The surface of particles will be adsorptive or functionalizable so as to bind, either directly or indirectly, an oligonucleotide or an sbp member. The nature of particles is described above.

Fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminostilbenes immines, anthracenes, oxacarboxyanine, merocyanine, 3-aminoequilenin, perylene, bis-benzoxazole, bis-p-oxazolyl benzene, 1,2-benzophenazine, retinal, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Additionally, energy absorbent or quenching particles can be employed which are solid insoluble particles of at least about 50 nm in diameter capable of quenching the fluorescence of the fluorescent particle when within the distance resulting from hybridization of a probe with the polynucleotide analyte or from specific binding between members of specific binding pairs. The quenching particle may be the same or different, usually different, from the fluorescent particle. Normally, the quenching particle will provide a substantial quenching at a distance of more than about 50 Å, preferably more than about 500 Å, more preferably more than about 2000 ÅA, where the distance is measured from the surfaces of the particles.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with oxilates, usually oxalyl, active esters, e.g., p-nitrophenyl and a peroxide, e.g., hydrogen peroxide, under basic conditions. Alternatively, luciferins may be used in conjunction with luciferase or lucigenins.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

Nucleoside triphosphates—a nucleoside having a 5' triphosphate substituent, preferably a deoxynucleoside triphosphate. The nucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof.

The derivatives and analogs are exemplified by those that are recognized and polymerized in a similar manner to the underivitized nucleoside triphosphates. Examples of such derivatives or analogs by way of illustration and not limitation are those which are modified with a reporter group, biotinylated, amine modified, radiolabeled, alkylated, and the like and also include thiophosphate, phosphite, ring atom modified derivatives, and the like. The reporter group can be a fluorescent group such as fluoroscein, a chemiluminescent group such as luminol, a terbium chelator such as N-(hydroxyethyl) ethylenediaminetriacetic acid that is capable of detection by delayed fluorescence, and the like.

Polynucleotide polymerase—a catalyst, usually an enzyme, for forming an extension of the polynucleotide primer along a DNA or RNA template including the single stranded polynucleotide where the extension is complementary thereto. The polynucleotide polymerase is a template dependent polynucleotide polymerase and utilizes the nucleoside triphosphates as building blocks for extending the 3'-end of the polynucleotide primer to provide a sequence complementary with the single stranded polynucleotide. Usually, the catalysts are enzymes, such as RNA polymerases, preferably DNA polymerases such as, for example, prokaryotic DNA polymerase (I, II, or III), T4 DNA polymerase, T7 DNA polymerase, Klenow fragment, reverse transcriptase, RNA replicases, and the like derived from any source such as cells, bacteria, such as E. coli, plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the viscosity conditions or stringency which include temperature, solvent ratios, salt concentrations, and the like.

First polynucleotide probe—a compound having a polynucleotide sequence at its 3'-end (3'-target binding sequence) at least a portion of such sequence, preferably all of such sequence, capable of hybridizing with a portion of the target polynucleotide analyte by virtue of being partially or completely, usually completely, complementary to a region of the target polynucleotide analyte such that the first polynucleotide probe will become bound to such region of the target polynucleotide analyte. The first polynucleotide probe also comprises a first flanking sequence that is at least 50% complementary, usually at least 65% complementary, to a second flanking sequence of a second polynucleotide probe. The first polynucleotide probe may contain additional sequences located between the target polynucleotide binding sequence and the first flanking sequence and attached to the first flanking sequence distal to the target polynucleotide binding sequence.

The major criteria for choosing the first polynucleotide probe are: (1) The 3'-end target binding sequence should be reliable, that is, it should be closely or exactly complementary with at least a portion of the target nucleotide sequence and should be of sufficient length to provide stable and specific binding. (2) The 3'-end must form, or be capable of forming, a free 3'-hydroxyl group. The minimum first flanking sequence will usually be at least 10, preferably at least 15, nucleotides in length. Additional sequences, usually located between the 3'-end target binding sequence and the first flanking sequence are selected to increase the distance between the two groups and thus provide for greater DNA synthesis during amplification and to provide for receptor binding sites to permit detection of the amplified product. In general, the first polynucleotide probe will be about 30 to 5,000 nucleotides, more frequently 40 to 1,000 nucleotides in length. The combined length of the hybridizing portion of the first and second polynucleotide probes is at least about 20 nucleotides, preferably about 40 to 2,000 nucleotides, in length. With biologically synthesized polynucleotides random fragments of unknown sequences may be used provided, however, that nucleic acids are single stranded and complementary to the target nucleotide sequences or the polynucleotide analyte.

Second polynucleotide probe—The second polynucleotide probe has a sequence at its 5'-end, at least a portion and preferably all of which is capable of hybridizing with the target polynucleotide analyte at a region other than that with which the first polynucleotide probe hybridizes (5'-target binding sequence). The second polynucleotide probe has a sequence that is at least 50% complementary, usually at least 65% complementary to the first flanking sequence of the first polynucleotide probe and is designated as the second flanking sequence. Thus, the first and second polynucleotide probes each have a polynucleotide sequence that is at least partially complementary to a sequence in the other. The second polynucleotide probe may contain additional receptor binding or spacer sequences located between the target polynucleotide binding sequence and the second flanking sequence and attached to the second flanking sequence distal to the target polynucleotide binding sequence.

The two regions of the target polynucleotide analyte complementary to the first and second polynucleotide probes will normally be in reasonable proximity to one another to ensure that a substantial fraction of the analyte will have the two regions linked. The two regions may be within 0 to 50 nucleotides, preferably 0 to 1 nucleotides. Where the regions are separated by more than one nucleotide, it will frequently be desirable to extend the first probe when bound to the target by means of a nucelotide polymerase and nucleoside triphosphates and thereby reduce the distance between the probes.

Non-contiguous—the probes are hybridized to non-contiguous portions of the target nucleotide sequence, there being at least one nucleotide present in the target polynucleotide sequence between the hybridized 5' terminus of the first polynucleotide probe and the 3'-end of the second polynucleotide probe.

Contiguous—the probes are considered to be contiguous when there are no nucleotides between the 5'-end of the first probe sequence and the 3'-end of the second probe sequence, when these nucleotide sequences are hybridized with the target polynucleotide analyte.

Copy—means a sequence that is a direct copy of a single stranded polynucleotide as differentiated from a sequence that is complementary to the sequence of such single stranded polynucleotide. In the present invention a complementary sequence of a single stranded polynucleotide is produced initially as the result of the extension of the polynucleotide primer and a sequence that is a direct copy of the single stranded polynucleotide is subsequently obtained from the aforementioned complementary sequence.

Covalently attaching—forming a chemical bond between the first polynucleotide probe and the second polynucleotide probe.

The chemical bond can be formed whether the probes are contiguous or not when the probes are bound to the target polynucleotide analyte, usually when separated by 0 or 1 nucleotide. Covalent attachment can be achieved enzymatically, for example by utilizing a ligase. Prior to ligating the probes, the probe having a 3' terminus extendable in the direction of the other probe hybridized with the target polynucleotide analyte may be treated to render it contiguous or effectively contiguous with the other probe. The probes are effectively contiguous, for example, when enzymatic ligation or a chemical coupling can take place. Generally, the probes are effectively contiguous when they are within 1 to 3 nucleotides apart. Chain extension may be achieved, for example, by adding a polynucleotide polymerase and nucleoside triphosphates or by ligating to one of the probes a nucleotide sequence complementary to the non-contiguous region of the target polynucleotide analyte between hybridized probes. The covalent attachment may be achieved chemically by forming chemical bonds between the phosphate moieties of the probes.

Means for extending a probe—in order to ligate the probes when the probes are bound with the target polynucleotide sequence it is often desirable to render the probes contiguous. As explained above, the probe having a 3'-terminus extendable in the direction of the other probe can be extended by combining the probe hybridized to the target polynucleotide analyte with a polynucleotide polymerase and nucleoside triphosphates under conditions for extending the probe. Alternatively, a nucleotide sequence complementary to the non-contiguous portion of the target polynucleotide analyte between the probes can be ligated to one of the probes.

One embodiment of the present invention concerns a method of producing at least one copy of a single stranded polynucleotide or of a sequence complementary thereto. The method comprises forming in the presence of nucleoside triphosphates and template dependent polynucleotide polymerase an extension of a polynucleotide primer having a sequence hybridizable with a first flanking sequence at the 3'-end of the single stranded polynucleotide, wherein the first flanking sequence is at least partially complementary with a second flanking sequence of the single stranded polynucleotide and dissociating the extended polynucleotide primer and the single stranded polynucleotide. The above steps are repeated to yield the appropriate copy.

Generally, a combination is provided in a liquid medium which comprises (1) a single stranded polynucleotide having a polynucleotide sequence flanked at each end by internally hybridizable first and second flanking sequences, (2) a polynucleotide primer at least a 10 base portion of which at its 3'-end is complementary to that member of the first and second flanking sequences that is at the 3'-end of the single stranded polynucleotide, (3) nucleoside triphosphates, and (4) template dependent polynucleotide polymerase. The combination is incubated under conditions for (1) dissociating any internally hybridized first and second flanking sequences, (2) hybridizing the polynucleotide primer with its complementary sequence, flanking the single stranded polynucleotide, (3) extending the polynucleotide primer along the single stranded polynucleotide to provide a first extended polynucleotide primer, (4) dissociating the first extended polynucleotide primer and the single stranded polynucleotide, (5) hybridizing the first extended polynucleotide primer with the polynucleotide primer, (6) extending the polynucleotide primer along the first extended polynucleotide primer to provide a second extended polynucleotide primer, (7) dissociating the second extended polynucleotide primer from the first extended polynucleotide primer, and (8) repeating steps (5)–(7) above.

An embodiment of the present invention is illustrated in FIG. 4 by way of example and not limitation.

Molecule I can be, for example, double stranded DNA having an inverted repeat with complementary sequences 1$a$ and 1$b$. The DNA can be rendered single stranded to yield molecule II, or molecule II can be RNA having sequences 1$a$ and 1$b$. Hybridization of polynucleotide primer 1$c$ with molecule II yields molecule III. Primer 1$c$ has substantially the same or a similar polynucleotide sequence as sequence 1$a$. In the presence of DNA polymerase and nucleoside triphosphates primer 1$c$ is extended along molecule II to yield molecule IV. Dissociation of molecule IV yields single stranded IVa and IVb. Molecule IVa is the unchanged molecule II and has complementary sequences 1$a$ and 1$b$ and molecule IVb has complementary sequences 1$c$ and 1$d$. As is evident 1$c$ corresponds to 1$a$, and 1$d$ corresponds to 1$b$. Polynucleotide primer 1$c$ can be hybridized to region 1$b$ of IVa and to region 1$d$ of IVb to yield molecules Va (III) and Vb, respectively. Extension of primer 1$c$ along Va and Vb under conditions described above yields molecules VIa (IV) and VIb, respectively. Molecules VIa and VIb can be dissociated to single stranded polynucleotides, which can then hybridize with primer 1$c$ and the chain extension can be repeated. In this way multiple copies of the initial single stranded polynucleotide encompassing the sequence between the sequences 1$a$ and 1$b$ of molecule II, and a sequence complementary thereto, can be obtained.

In carrying out the method an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of about 5.5–8.5, and preferably in the range of about 6–8. The pH and temperature are chosen and varied, as the case may be, so as to provide for either simultaneous or sequential dissociation of any internally hybridized sequences in the single stranded polynucleotide sequence, hybridization of the polynucleotide primer with the single stranded polynucleotide, extension of the primer, dissociation of the extended primer, hybridization of extended primer with primer, extension of the so-hybridized primer, and dissociation of extended primer. In some instances, a compromise will be made between these considerations depending on whether the above steps are performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. Desirably constant temperatures during the period for conducting the method will be used but frequently the medium will be cycled between two or three temperatures. When constant, the temperature will be near the melting temperature of the complex of the single stranded polynucleotide and the extended polynucleotide primer. The temperatures for the method will generally range from about 10° to 100° C., more usually from about 20° to 95° C., preferably 35° to 70° C. However, the temperature can be varied depending on whether the above steps are carried out sequentially or simultaneously. For example, relatively low temperatures of from about 20° to 40° C. can be employed for the extension steps, while denaturation and hybridization can be carried out at a temperature of from about 50° to 95° C.

The time period for carrying out the method of the invention will generally be long enough to achieve a desired number of copies of the single stranded polynucleotide or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 1 to 80, frequently 20–80. As a matter of convenience it will usually be desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer.

The amount of the single stranded polynucleotide which is to be copied can be as low as one or two molecules in a sample but will generally vary from about $10^2$ to $10^{10}$, more usually from about $10^3$ to $10^8$ molecules in a sample. The amount of the polynucleotide primer will be at least as great as the number of copies desired and will usually be $10^{-15}$ to $10^{-9}$ moles per sample, where the sample is 10–1,000 $\mu$L. Usually, the primer will be present in at least $10^{-12}$M, preferably $10^{-10}$M, and more preferably at least about $10^{-8}$M. Preferably, the concentration of the polynucleotide primer is substantially in excess over, preferably at least 100 times greater than, the concentration of the single stranded polynucleotide.

The final concentration of each of the reagents will normally be determined empirically to optimize the number of the copies of the target sequence.

The concentration of the deoxynucleoside triphosphates in the medium can vary widely; preferably, these reagents are present in an excess amount. The deoxynucleoside triphosphates will usually be present in $10^{-6}$ to $10^{-2}$M, preferably $10^{-5}$ to $10^{-3}$M.

The concentration of the template-dependent polynucleotide polymerase will usually be determined empirically. Preferably, a concentration will be used that is sufficient such that further increase in the concentration will not decrease the time for the amplification by over 5-fold, preferably 2-fold. The primary limiting factor generally is the cost of the reagent.

The order of combining of the various reagents to form the combination may vary. Generally, a single stranded polynucleotide with first and second flanking sequences is itself the target polynucleotide sequence in the sample or is formed as a function of the presence of a polynucleotide analyte in the sample. This may be combined with a pre-prepared combination of polynucleotide primer, nucleoside triphosphates, and template-dependent polynucleotide polymerase. However, simultaneous addition of the above, as well as other step-wise or sequential orders of addition, may be employed.

The concentration and order of addition of reagents and conditions for the method are governed generally by the desire to maximize the number of copies of the single stranded polynucleotide sequence and the rate at which such copies are formed. Generally, it is desirable to increase the number of copies of the single stranded polynucleotide sequence by at least a factor of $10^2$, preferably a factor of $10^4$, more preferably $10^6$ or more.

The present invention has particular application to the determination or detection of a polynucleotide analyte in a sample. In general, the method comprises forming as a result of the presence of an analyte a single stranded polynucleotide flanked by first and second polynucleotide flanking sequences. Multiple copies of the single stranded polynucleotide are then made. Directly or indirectly detecting the thus formed single stranded polynucleotide indicates the presence of the analyte.

The single stranded polynucleotide can be formed by contacting the sample with first and second polynucleotide probes. The first probe comprises a sequence at its 3'-end complementary to a first portion of one strand of the analyte and a first flanking sequence. The said second probe comprises a sequence at its 5'end complementary to a second portion of the same strand of the analyte and a second flanking sequence. The first and second flanking sequences are at least 50–65% complementary with each other and will frequently be 80–100% complementary. The contact is carried out under conditions for binding of the first and second probes with the analyte. Then, conditions are provided for ligating the first and second polynucleotide probes to one another only when bound to said analyte.

The order of combining of the various reagents to form the combination may vary and can be concomitant or simultaneous or wholly or partially sequential. Generally, a sample containing an analyte sequence is obtained. This may be combined with a pre-prepared combination of first and second polynucleotide probes, nucleoside triphosphates, and polynucleotide polymerase, followed by addition of a ligase. However, simultaneous addition of the above, as well as other step-wise or sequential orders of addition, may be employed. The concentration and order of addition of reagents and conditions for the method are governed generally by the desire to optimize hybridization of all the target polynucleotide sequences with the first and second polynucleotide probes and covalent attachment of the so-hybridized first and second polynucleotide probes.

One means for covalently attaching the first and second probes when these probes are hybridized with the target polynucleotide sequence involves the chain extension of the first probe to render the first and second polynucleotide probes contiguous. One means for extending the first probe comprises adding a polynucleotide polymerase and deoxynucleoside triphosphates to the liquid medium and incubating the medium under conditions for forming a chain extension at the 3'-end of the first probe to render it contiguous with the second polynucleotide probe when these probes are hybridized with the analyte.

When the first and second polynucleotide probes are rendered contiguous when hybridized with the analyte sequence, the first and second probes are then covalently attached. One method of achieving covalent attachment of the first and second polynucleotide probes is to employ enzymatic means. Preferably the medium containing the first and second polynucleotide probes hybridized with the analyte sequence can be treated with a ligase, which catalyzes the formation of a phosphodiester bond between the 5' end of one probe and the 3' end of the other.

Any enzyme capable of catalyzing the reaction of the polynucleotide 3'-hydroxyl group can be employed. Examples, by way of illustration and not limitation, of such enzymes are polynucleotide ligases from any source such as *E coli* bacterial ligase, T4 phage DNA ligase, mammalian DNA ligase, and the like. The pH, temperature, solvent, and time considerations will be similar to those described above for the method of the invention.

Another means for achieving the covalent attachment of the first and second polynucleotide probes when the probes are hybridized to non-contiguous portions of the analyte sequence involves the use of a nucleotide sequence that is sufficiently complementary to the non-contiguous portion of the analyte sequence lying between the first and second nucleotide probes. For purposes of this description such a nucleotide sequence will be referred to as an intervening linker sequence. The linker sequence can be prepared by known methods such as those described above for the preparation, for example, of the first and second polynucleotide probes. The linker sequence can be hybridized to the analyte sequence between the first and second polynucleotide probes. The linker sequence can then be ligated to both the first and second polynucleotide probes utilizing enzymatic means as referred to above. It is also possible to utilize combinations of linker sequences and polymerase to achieve a contiguous relationship between the first and second polynucleotide probes when these sequences are bound to the analyte.

Following ligation of the first and second polynucleotide probes when these probes are hybridized with the polynucleotide analyte, the hybridized polynucleotides are dissociated. Because each of the probes contains a flanking sequence that is potentially hybridizable with a flanking sequence in the other, the single stranded polynucleotide also contains these sequences. Multiple copies of the single stranded polynucleotide resulting from the ligated probes are then prepared. In one approach multiple copies of the single stranded polynucleotide are obtained by the procedures described above using a single polynucleotide primer. In another approach multiple copies of the single stranded polynucleotide are obtained by using the double primer technique described in U.S. Pat. Nos. 4,683,195 and 4,683,202, the disclosures of which are incorporated herein by reference. In still another approach amplification can be achieved as described in U.S. patent application Ser. No. 076,807 filed Jul. 23, 1987 now U.S. Pat. No. 4,994,368, the disclosure of which is incorporated herein reference. It will be appreciated by those skilled in the art that other methods of forming multiple copies can be used in the present invention for detection of an analyte.

Detection of the first flanking sequence linked to the second flanking sequence or the detection of the single stranded polynucleotide or its complementary sequence indicates the presence of the polynucleotide analyte in the sample.

An example of the determination of a polynucleotide analyte is illustrated, by way of example and not limitation, in FIG. 2.

The polynucleotide analyte is represented in VII wherein two polynucleotide probes are hybridized to a portion of the target analyte. The probes respectively contain sequences $2a$ and $2b$ that are at least partially complementary to one another. Molecule VII is treated to render the probes ligatable and to ligate the probes. This can be accomplished as described above and is depicted as molecule VIII in FIG. 5. Dissociation of VIII yields molecule IX, which is a single stranded polynucleotide having two at least partially complementary sequences, $2a$ and $2b$. As can be seen, molecule IX is similar to molecule II in FIG. 4 and can be combined with a polynucleotide primer $2c$, which hybridizes with sequence $2b$ of molecule IX to give molecule X. Chain extension of primer $2c$ as described above yields molecule XI. Dissociation of XI followed by hybridization with primer $2c$ and chain extension yields multiple copies of molecule IX or a sequence complementary thereto. The single stranded polynucleotide is detected either as a single strand or hybridized with its complementary strand. The presence of ligated probes indicates the presence of the polynucleotide analyte in the sample.

In carrying out the method of the invention as applied to the detection of a polynucleotide analyte, an aqueous medium is employed, which may further contain other polar solvents as described above. The pH, temperature, time, and concentration of reagents generally will be those described above for the formation of multiple copies of a single stranded polynucleotide.

The pH for the medium will usually be in the range of about 4.5 to 9.5, more usually in the range of about 5.5–8.5, and preferably in the range of about 6–8.

The temperatures for the method will generally range from about 20° to 90° C., more usually from about 30° to 70° C. preferably 37° to 50° C.

Generally, the time period for conducting the method will be from about 5 to 200 min. As a matter of convenience, it will usually be desirable to minimize the time period.

The concentration of the target polynucleotide analyte can be as low as possibly one molecule, preferably at least $10^{-21}$M in a sample but will generally vary from about $10^{-14}$M to $10^{-19}$M, more usually from about $10^{-16}$ to $10^{-19}$M. The concentration of the first and second polynucleotide probes and the deoxynucleoside triphosphates in the medium can vary widely. Preferably, these reagents will be present in large molar excess over the amount of target analyte expected. The deoxynucleoside triphosphates will usually be present in $10^{-6}$ to $10^{-2}$M, preferably $10^{-5}$ to $10^{-3}$M. The second polynucleotide probe, as well as the first polynucleotide probe, will usually be present in at least $10^{-12}$M, preferably $10^{-10}$M, more preferably at least about $10^{-8}$M.

The concentration of the polymerase and any cofactors in the medium can also vary substantially. These reagents may be present in as low as $10^{-12}$M but may be present in a concentration at least as high or higher than the concentration of the first and second nucleotide probes.

While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of a single stranded polynucleotide be produced in relation to the polynucleotide analyte sequence so that such copies can be readily detected and provide an accurate determination of the polynucleotide analyte.

After the medium is incubated either concomitantly or sequentially under the above conditions any single stranded polynucleotide or ligated target binding sequences of the first and second probes present are detected. The presence of the ligated sequences indicates the presence of the polynucleotide analyte in the sample. The ligated sequences can be detected in numerous ways.

In the present method, some of the molecules of the polynucleotide primer can be labeled with a ligand (B) and other of the molecules of the polynucleotide primer can be labeled with a detectable (F) label. The ligand can be a small organic molecule, a polynucleotide sequence, a protein, or the like. Upon amplification, a mixture of duplexes is obtained (See FIG. 6), some having ligand at both ends, some having detectable label at both ends, and some having ligand at one end and detectable label at the other. The ratios of the products can be modified by varying the ratio of the two differently labeled primers. The duplexes can be detected by causing the molecule to bind to a surface to which is bound a receptor for the ligand. Duplexes containing the two primer labels that are shorter than the single stranded polynucleotide with its first and second flanking sequences can be prevented from binding by using conditions that are stringent enough to dissociate only these shorter duplexes. After removal of unbound material, the support is examined for the presence of a detectable label. The presence thereof indicating the presence of polynucleotide analyte in the sample.

In another approach, the internally hybridizable sequences can be selected because a synthetic or natural receptor exists that can bind to the hybridized sequences. The sequences will usually be introduced by including them between the target polynucleotide binding sequence and a flanking sequence of a polynucleotide probe or the single stranded polynucleotide. Alternatively, they can be introduced as labels at the 5'-end of a portion of the polynucleotide primer molecules. The tetracycline repressor is such a receptor. This protein binds to the tetracycline operator and the hybridized sequences can be selected to comprise some or all of this operator. The repressor is bound to a solid support and used to absorb and concentrate the amplification product from the amplification reaction solution. The bound product can then be detected by staining with a dye such as acridinium orange, by changes in a physical property of the adsorbent such as electrical properties, optical properties, acoustic wave modulation, and the like, or by detecting the presence of a label bound to another portion of the polynucleotide primer molecules.

Other operator-repressor pairs can be used including, for example, the lac repressor and operator which have been used as a ligand and receptor for capture of DNA duplexes and the tryptophane repressor and operator.

In another approach bromodeoxyuridine can be incorporated into a portion of the polynucleotide primer molecules and antibodies to bromodeoxyuridine can be employed. Detection of the bound sequence can be accomplished by any of the above methods.

In a preferable approach for detection of the single stranded polynucleotide, the polynucleotides are simultaneously or sequentially denatured by heating or use of denaturing solvents and solutes and caused to bind to a support by, for example, one of the above methods. The support is then contacted with a probe comprised of a nucleic acid sequence and a label or receptor binding site. The nucleic acid sequence is complementary to at least the portion of the single stranded polynucleotide that was ligated, or its complementary sequence. The presence of the single stranded polynucleotide is then indicated by the presence of the label or receptor binding site on the support.

In another assay format (as depicted in FIG. 7), the single strand polynucleotide containing the internally hybridizable sequences 3a and 3b can be used as a label. In this method, any means, such as formation of a DNA sandwich, can be used to cause a labeled nucleic acid strand to bind to a surface. In the sandwich method, two probes are used that can bind to a target analyte. One of these probes is bound or can be caused to bind to a solid surface, for example, by the use of legand-receptor binding, such as biotin-avidin. The other probe carries the single stranded polynucleotide as a label. After (1) hybridization of the probes with the target polynucleotide sequence, (2) binding of the complex to the surface when one of the probes is not already bound, and (3) washing of the surface, the single stranded polynucleotide is caused to initiate the present amplification process and the products are detected by any convenient method of detecting specific polynucleotide sequences, including the above described methods for detecting the single stranded polynucleotide.

Any standard method for specifically detecting double strand nucleic acid sequences can be used.

One method for detecting nucleic acids is to employ nucleic acid probes. This method generally involves immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about ten minutes to forty-eight hours.

After the above time period, the solid support is washed several times to remove unbound probe and the hybridized material is detected by autoradiography or spectroscopic methods.

One method utilizing probes is described in U.S. patent application Ser. No. 773,386, filed Sep. 6, 1985 now U.S. Pat. No. 4,860,104, the disclosure of which is incorporated herein by reference. The method comprises combining in an assay medium the sample and first and second polynucleotide reagents complementary to the nucleic acid fragment. Each of the first and second reagents hybridize with a different region of nucleic acid fragment. The first reagent contains means for rendering the first reagent non-covalently polymerizable. The second reagent contains means for rendering the second reagent detectable. The sample and the first and second reagents are combined in the assay medium under conditions for polymerizing the first reagent wherein the second reagent becomes bound to the polymerized first reagent only when the DNA fragment is present in the sample. A determination is then made as to whether the second reagent has become bound to the polymerized first reagent.

In order to separate the single stranded polynucleotide from other components in an assay mixture containing a sample it can be desirable, and indeed preferable in some circumstances, that the first or second polynucleotide probe or the single stranded polynucleotide has, or is capable of having, means for immobilizing the sequence. Generally, this means for immobilizing involves a support. The sequence in question can be treated to bind the sequence to a support prior to the use of this sequence in the method of the present invention. Numerous methods are known for binding nucleotide sequences to solid supports. For example see T. Goldkorn et al., *Nucleic Acids Research* (1986) 14:9171–9191 and the references contained therein. Generally, the procedures for attaching the nucleotide sequence to supports involve chemical modifications of some of the nucleotides in the sequence whereby the sequence can then be attached to the support. Preferably, the bond between the support and the nucleotide sequence will be covalent, more preferably involving a linking group between the nucleotide sequence the support. For example, the support can be treated to introduce maleimide groups and the nucleotide sequence can be treated to introduce a thiol group. The thiol group is reactive with the activated olefin of the maleimide group and in such a fashion the nucleotide sequence can be covalently bound to the support. Examples of other such linking groups are cellulose derivatized with diazobenzyloxymethyl groups as described by Noyes, B. E. and Start, G. R., *Cell* 5, 301 (1975) and Alwine, J. C., et al., *Proc. Natl. Acad. Sci.*, U.S.A. 74, 5350 (1977), and cellulose derivatized with o-aminophenylthioether, such as described by Seed, B., *Nucleic Acids Res.*, 10, 1799 (1982).

If the nucleotide sequence is not initially bound to a support, it may be desirable that one of the two sequences become bound to a support at some time during the method of the invention, preferably, prior to the determination of whether the first and second target polynucleotide binding sequences have become covalently attached as a result of the presence of the polynucleotide analyte. Accordingly, the support and one of the nucleotide sequences must contain reactive groups which can provide a linkage between the support and the nucleotide sequence. The nature of the reactive groups will be such as to be compatible with the method of the present invention.

One such system is that described above where the support would contain maleimide groups and the nucleotide sequence would contain a thiol group. In another embodiment the nucleotide sequence and the support can contain complementary specific binding pair members such as biotin-avidin and the like. Thus, the method of the present invention can be run in solution and at the appropriate time the support can be introduced whereupon the complementary sbp members will bind. After the support is washed, to remove unbound material, further reactions or determinations can be carried out.

Other examples of such systems are repressor-operator interactions where one of the nucleotide sequences is captured at the solid surface by its sequence specific interaction with a specific repressor or modulator protein immobilized on the solid surface. An advantage of this embodiment of the capture phase is that in some cases release of the operator DNA from the repressor can be accomplished by treating the complex with an inducer molecule. For example, the tetracycline repressor may be immobilized on a solid surface so that an operator sequence present on one or the other of the nucleotide sequences is specifically captured and retained when the solution is contacted to the surface. The surface may then be washed to eliminate any non-specific binding and finally the operator containing nucleotide may be released from the surface by contacting the repressor-operator complex bound at the surface with an inducer molecule (tetracycline or one of its active analogs in this case).

The inducer molecule may be the "natural inducer" in the sense that it is structurally identical with the molecule in nature that causes dissociation of the biological/regulatory repressor-operator complex or it may be a synthetic analog of the natural inducer with similar or enhanced binding and complex dissociation activity. Examples of the above include the tetracycline repressor-operator interaction and its dissociation by tetracycline such as described by Hillen, W., et al., *J. Mol. Biol.*, 169, 707–721 (1983) and Klock, G., et al., *J. Bact.*, 161, 326–332 (1985).

In the situation where the nucleotide sequence is covalently attached to the support, it may be desirable to remove the attached sequence from the support, such as, for example, in order to amplify or clone the sequence. In this situation it is desirable to introduce a cleavable group between the nucleotide sequence and the support. Exemplary of such cleavable groups are pyrophosphate linkages, disulfide linkages and restriction enzyme cleavage sites.

After provision has been made for covalently attaching the first and second polynucleotide probes when these sequences are hybridized with the polynucleotide analyte to produce a single stranded polynucleotide and after amplification of the single stranded polynucleotide if present, the presence of covalently attached first and second target polynucleotide binding sequences is determined. The presence of covalent attachment indicates the presence of the polynucleotide analyte in the sample. As mentioned above this determination may involve a nucleotide sequence bound, or capable of becoming bound, to a support. The support is removed from the medium, washed free of unbound material, and then examined for the coupled first and second target polynucleotide binding sequences, for example, by detecting the presence of a label or a reporter group. Generally, this examination involves contacting the support with the remaining members of a signal producing system in order to produce a signal in relation to the presence of the target nucleotide sequence in the sample.

Use of the method in accordance with the present invention allows a support to be washed under conditions that would normally be more vigorous than those used when hybridization is carried out without covalent attachment. Frequently, the washing conditions will completely disassociate duplexes bound to the support. These conditions include solutions containing kaotropic agents such as urea either alone or in combination with other denaturants such as formamide used either at ambient or elevated temperature. The covalent attachment between the first and second polynucleotide probes and the bonding of one of the probes to a surface, however, will be unaffected. Detection of the resulting labelled material bound to the support will indicate the presence of the target nucleotide sequence in the sample.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Another aspect of a method for detecting the presence of a polynucleotide analyte in a sample suspected of containing the analyte involves ligating third and fourth sequences of a polynucleotide probe, where the third and fourth sequences are hybridizable to separate portions of the analyte and ligatable, or capable of being rendered ligatable, only in the presence of the analyte. When the third and fourth sequences are ligated, the thus formed single stranded polynucleotide can be incorporated into a circular polynucleotide strand. The polynucleotide probe further comprises at least partially complementary first and second sequences.

An extension of a polynucleotide primer is formed in the presence of nucleoside triphosphates and template dependent polynucleotide polymerase. At least the 3'-end of the polynucleotide primer can hybridize with the first or second sequences of the polynucleotide probe. Next, extended polynucleotide primer and/or a sequence identical to and/or complementary with at least that portion of the ligated third or fourth sequences complementary to the separate portions of said analyte are detected. The presence of any one of the above indicates the presence of polynucleotide analyte in the sample.

Various techniques can be employed for preparing a polynucleotide primer, first and second polynucleotide probes, or a single stranded polynucleotide sequence in accordance with the present invention. They can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The polynucleotide primer can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as those employed in commercial kits for preparation of RNA (e.g. from Promega) and by the use of M13 for single stranded DNA as described by J. Messing (1983) *Methods Enzymol*, 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

The single stranded polynucleotide or the first and second polynucleotide probes can be prepared by enzymatic ligation. Two appropriate complementary oligonucleotides can be synthesized by standard automated techniques. They are then enzymatically ligated to another polynucleotide sequence, for example, by T4 ligase, to produce the single stranded polynucleotide or each individually ligated to different polynucleotide sequences, the latter each being hybridizable with a portion of a polynucleotide analyte. Desired products can then be isolated, for example, by polyacrylamide gel electrophoresis or high performance liquid chromatography (HPLC).

In some instances, the 3'-end of the single stranded polynucleotide or of the second polynucleotide probe will be modified to prevent reaction with template dependent DNA polymerase or to append a binding sequence. The 3'-end can, for example, be modified by ligation of a dideoxynucleotide or a ribonucleotide followed by oxidation of the ribose with periodate followed by reductive amination of the resulting dialdehyde with borohydride and a bulky amine such as aminodextran.

The polynucleotide primer can be prepared by standard automated techniques.

As a matter of convenience, the reagents employed in the present invention can be provided in a kit in packaged combination with predetermined amounts of reagents for use in the present method. In assaying for a polynucleotide analyte in a sample, a kit useful in the present method can comprise in packaged combination with other reagents a polynucleotide primer and first and second polynucleotide probes, which can be labeled or one of which can be bound to a support or can be provided with groups to render the sequence labeled or bound to a support. For use in a method of producing multiple copies of a single stranded polynucleotide, the kit will contain a polynucleotide primer. Either of the kits above can further include in the packaged combination nucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include a polynucleotide polymerase and also means for covalently attaching the first and second sequences, such as a ligase, and members of a signal producing system.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where reactivity and shelf life will permit.

EXAMPLES

The invention is demonstrated further by the following illustrative examples.

Example 1

Single primer polynucleotide amplification of a single-stranded polynucleotide with flanking first and second complementary sequences (Oligomer 1)

Oligodeoxyribonucleotide sequences 1, 2, 3, 4, 5, 6, 7, 8 & 9:

Single-stranded polynucleotide with first and second flanking sequences:
Oligomer 1
5' CAA TTA CAC AAG CTT AAT ACA TTC CTT CGA GCT CGG TAC CCG GGG ATC CTC TAG AGT CGA CCT GCA GGC ATG CAA GGA ATG TAT TAA GCT TGT GTA ATT G 3'
First polynucleotide probe A;
Oligomer 2
g' CAA TTA CAC AAG CTT AAT ACA TTC CTT CGA GCT CGG TAC CCG GGG ATC CT3'
First polynucleotide probe B;
Oligomer 3
5' CAA TTA CAC AAG CTT AAT ACA TTC CTT CGA GCT CGG TAC CCG GGG ATC C 3'
Second polynucleotide probe;
Oligomer 4
5' CTA GAG TCG ACC TGC AGG CAT GCA AGG AAT GTA TTA AGC TTG TGT MAT TG 3'
Polynucleotide primer;
Oligomer 5
5' CAA TTA CAC AAG CTT AAT ACA TTC C 3'
Oligomer 6
5' CCG GGG ATC CTC TAG AGT CGA CC 3'
Oligomer 7
5' CCG GGG ATC CCT AGA GTC GAC C 3'
Oligomer 8
5' TCT AGA GTC GAC CTG CAG GCA TGC A 3'
Oligomer 9
5' TGC ATG CCT GCA GGT CGA CTC TAG A 3' were synthesized by the phosphoramidite method and purified on denaturing polyacrylamide gels. The 27 5' terminal bases and the 27 3' terminal bases of the 100 mer oligomer 1 are self-complementary and therefore this molecule will form a "hairpin" or stem-loop structure. Oligomers 2 and 4 represent the 5' 50 bases and 3' 50 bases of oligomer 1, respectively. Oligomer 5 is complementary to the 3'terminal 25 bases of oligomers 1 and 4. Oligomers 6 (7) will hybridize to the central 23 (22) bases of oligomer 1, but oligomer 7 has a single base deletion (a thymidine residue). Oligomers 8 and 9are complementary; oligomer 8 is identical to oligomer 1 from bases 50 to 74 of oligomer 1, inclusive.

A protocol for DNA amplification of oligomer 1 using oligomer 5 as the polynucleotide primer is described; variations of this protocol will be described in later examples. One picomole (pmole) of oligomer 1 and 60 pmoles of oligomer 5 are combined in a buffer of 50 mM Tris-HCl (pH 8.4 @ 25° C.), 50 mM KCl, 2.5 mM Mg $Cl_2$, 0.2 mg/mL gelatin with 10 nanomoles (nmoles) each dNTP. Five units of Taq polymerase enzyme is added for a final volume of 50 microliters. Temperature cycling of 94° C. (1 minute), 37° C. (2 minutes), and 72° C. (3 minutes) is performed using a programmable thermal cycler (Ericomp, Inc.) for a number of cycles through the 3 temperatures. Aliquots from these reactions are withdrawn at various stages and dot-blotted onto GeneScreen Plus® nylon membranes (Du Pont) using protocols recommended by the manufacturer.

The dried membranes are prehybridized for 3 hours at 65° C. in a solution of 0.75M NaCl, 0.15M Tris-HCl (pH8.0), 10 mM EDTA, 5× Denhardt's solution (1 g Ficoll, 1 g polyvinyl pyrrolidone, 1 g BSA in a total vol 1000 ml $H_2O$), 20 mM sodium phosphate, 250 mg/mL sheared denatured calf thymus DNA, and 0.5% SDS. In order to assay for the formation of amplified oligomer 1, $^{32}$P5' end-labeled oligodeoxynucleotide probe (~10' DPM, 100–1000 Ci/mmole) is added with fresh prehybridization solution and hybridized overnight with gentle agitation at 60° C. The hybridized membranes are typically washed in a buffer of 0.3M NaCl, 0.06M Tris-HCl (pH 8.0), 4 mM EDTA, and 0.5% SDS at 60° C. for 30 minutes with one change of wash buffer. Washed membranes are exposed to Kodak X-Omat® AR film for varying lengths of time, sometimes with a single intensifying screen (Du Pont Cronex® Lightning-Plus).

FIG. 1 shows the results of amplification of 1 pmole of oligomer 1 in the presence of 60 pmoles of polynucleotide primer, oligomer 5. The probe in this case is oligomer 5 and the standards (Lane A, 1–10) are varying amounts of oligomer 1. No detectable hybridization occurs if oligomer 5 is left out of the amplification reaction. A small amount of amplification of oligomer 5 is detected when oligomer 1 is not added.

This blot was stripped of radioactive probe by washing for 10 minutes at room temperature in 0.4N NaOH and neutralizing in 1M Tris-HCl (pH 7.5), 0.3M NaCl, 4 mM EDTA. The membrane was then hybridized to 5'$^{32}$P-labeled oligomer 9 (see FIG. 2). In this case, amplification is detected in the reaction containing both oligomers 1 and 5 and not in those containing either 1 or 5 separately.

FIG. 1

Dot-blot hybridization of $^{32}$P oligomer 5 to single primer polynucleotide amplification products Row A. Lanes 1–10—Standards of 1.8, 0.9, 0.454, 0.18, 0.09, 0.045, 0.018, 0.009, 0.0045, 0.0018 nmoles oligomer #1.

Row A. Lane 11—Negative control of 1 μg sheared, denatured calf thymus DNA.

Row B. Lanes 7–11—Five μL aliquots from the 10, 20, 30, 40, and 50th temperature cycle of amplification reaction containing 60 pmoles of oligomer 5 with no oligomer 1. Note some hybridization of products from cycle 50 to the oligomer 5 probe.

Row C. Lanes 1–5—5 μL aliquots from the 10, 20, 30, 40 and 50th cycle containing oligomer 1 only (1 pmole). Note absence of detectable amplification product.

Row C. Lanes 7–11—5 μL aliquots from the 10, 20, 30, 40, and 50th cycle containing both oligomers 1 and 5. Amplification exceeds 2000-fold (1 pmole to >1.8 nmoles).

FIG. 2

Dot-blot hybridization of $^{32}$P oligomer 9 to single primer polynucleotide amplification products The blot in FIG. 1 was stripped of hybridized $^{32}$P oligomer 5 and hybridized to $^{32}$P oligomer 9 probe. Results are essentially as in FIG. 1 except that hybridization in row B, lanes 7–11, cannot be detected with this probe.

Example 2

Single primer polynucleotide amplification of cloned DNA from Neisseria gonorrhoeae
Oligodeoxyribonucleotide sequences 1, 2, 3, 4, 5:

Single-stranded polynucleotide target;
Oligomer 1

5'ACT TGG GCT ATC ACT TCC CTG AAC CGC GTG CTT TTA CTA ATA GAG AAC GAG CAA GGC TTC AAA GTT TTC CTG ATG ATT TTG AGT TTG TCG GAT CAA CAA CTG AAG T 3'

First polynucleotide substrate;
Oligomer 2

5' ACG GTT CCA TCA AAA GGG GGG AAT TCA CTT TTC TCT ATC ACT GAT AGG GAG TGG TM AAT AAC TCT ATC AAT GAT AGA GAC TTC AGT TGT TGA TCC GAC TTC GAAM GAG C

Second polynucleotide substrate;
Oligomer 3

5' ACG GTT CCA TCA AAA GGG GGG AAT TCT GTG TGG AAT TGT GAG CGG ATA ACA ATT TCA CAC AAC TTG GGC TAT CAC TTC CCT GGA TCC CCA T 3'

Polynucleotide primer;
Oligomer 4

5' ACG GTT CCA TCA AAA GGG GG

Polynucleotide probe;
Oligomer 5

5' TM TAG AGA ACG AGC AAG GCT TCA A 3'

Oligomer 1 is one strand of a double-stranged Rsa I restriction fragment from a N. gonorrhoeae (N. g.) genomic clone. The total cloned DNA insert represents a 7 kilobase (Kb) Sau 3AI restriction fragment originating from N. g. strain 125. This 7 Kb fragment was inserted into Bam HI linearized vector pGEM 3Zf(+) from Promega Biotech.

The 3'terminal twenty base of oligomer 1 hybridizes to bases number 80–99, inclusive, of oligomer 2 (see FIG. 8, A). This forms a primed substrate for DNA polymerization upon the oligomer 2 template from the 3' terminus of oligomer 1, catalyzed by Taq polymerase. The 185-base long product of this polymerization, when rendered single-stranded by the thermal denaturation, base pairs with its 3' terminal twenty bases to oligomer 4 (FIG. 8, B). This is a substrate for Taq polymerase which polymerizes upon the primed 185-base template to form a complementary strand product of 185 bases.

The denatured product of the preceding polymerization has twenty bases at its 3' terminus which hybridizes to oligomer 3 at nucleotides 62–81, inclusive, and therefore is a substrate for Taq polymerase to extend 61 bases upon the oligomer 3 template (FIG. 8, C). The product, when thermally denatured, produced 246-base long polynucleotide 6 of Scheme 5.

Polynucleotide 6 forms a stem-loop structure with a stem of 20 base pairs of complementary sequence at the 5' and 3' termini. It follows that the complement of 6 also forms a stem-loop structure. Both 6 and its complement hybridizes to primer oligomer 4 at their respective 3' terminus, providing a substrate for Taq polymerase and thereby allowing single primer polynucleotide amplification of the type described in Example 1. To summarize, the presence of oligomer 1 has allowed, by alternative polymerase extension of primed templates and thermal denaturation, the "linking" of sequences complementary to oligomers 2 and 3 forming polynucleotide 6.

The following experiment is an example of this technology. Five assays were performed containing the following components:

| Assay No. | 10 X Buffer | dATP dCTP dGTP dTTP (nmoles) | Oligomer 4 | Oligomer 2 | Oligomer 3 | Rsa I Digest of N. q. Genomic Clone | 5 Units TAQ Polymerase |
|---|---|---|---|---|---|---|---|
| 1 | + | 100 ea. | 18 pmoles | 20 pmoles | 20 moles | None | + |
| 2 | + | 100 ea. | 18 pmoles | 20 pmoles | 20 pmoles | 25 fmoles | + |
| 3 | + | 100 ea. | 18 pmoles | 200 fmoles | 200 fmoles | 25 fmoles | + |
| 4 | + | 100 ea. | 18 pmoles | 2 fmoles | 2 fmoles | 25 fmoles | + |
| 5 | + | 100 ea. | 18 pmoles | 20 pmoles | 20 pmoles | 25 amoles | + |

Ten times (10×) buffer is 0.1M Tris-HCl, pH 8.4 (at 25° C.), 0.5M KCl, 60 mM MgCl$_2$, 2 mg/mL gelatin. Final volume of assay was 100 μL. All components, except Taq polymerase, were added to eppendorf tubes, overlaid with 50 μL mineral oil and heated 95° C. for 3 minutes. Tubes were then allowed to slow cool over 30 minutes to less than 50° C. Five unites of Taq polymerase were then added and thermal cycling was begun in an ERICOMP thermal block: 94° C. for 30 sec, 50° C. for 30 sec, 72° C. for 2 min, then repetition of this three-temperature regimen (1 cycle). Ten microliter aliquots of these five assays were withdrawn at 20, 40, and 60 cycles and frozen.

Five microliters of the frozen aliquots were thawed and analyzed by dot-blotting onto Genescreen Plus™ nylon membranes (DuPont) using protocols recommended by the manufacturer. The blots were processed as described in Example 1. The $^{32}$P-kinased probe oligomer 5 (100–1000 Ci/mmole, ~10$^7$ dpm) was used to hybridize to the dot blot. Oligomer 5 is identical to bases 38–62, inclusive, of the target oligomer 1.

The blot in FIG. 3 demonstrates that by 60 temperature cycles, all assays containing target DNA had greater than 25 fmoles/5 μL of DNA hybridizable to the probe. In dot blot 5E, this represents an amplification of $5 \times 10^{-18}$ moles hybridizable sequence to $>25 \times 10^{-15}$ moles hybridizable sequence, or about a $5 \times 10^3$-fold amplification.

FIG. 3 Legend

Dot-blot Hybridization of $^{32}$P Oligomer 5 to Amplification Products of Assays 1–5

Row A. Lanes 1–4—Standards of 25, 2.5, 0.25, and 0.025fmoles N. gonorrhoeae genomic clone.
Row C. Lanes 1–5 Five microliter aliquots of 20th temperature cycle of assays 1–5, respectively.
Row D. Lanes 1–5—Five microliter aliquots of 40th temperature cycle of assays 1–5, respectively.
Row E. Lanes 1–5—Five microliter aliquots of 60th temperature cycle of assays 1–5, respectively.

What is claimed is:

1. A kit for use in determining a polynucleotide analyte, which comprises in packaged combination:

a first polynucleotide probe having a first nucleotide sequence capable of hybridizing to a first portion of said polynucleotide analyte, a second polynucleotide probe having a second nucleotide sequence capable of hybridizing to a second portion of the same strand of said polynucleotide analyte other than with the portion recognized by said first nucleotide sequence of said first polynucleotide probe, said first polynucleotide probe and said second polynucleotide probe each comprising a sequence of nucleotides that are hybridizable with one another when said first nucleotide sequence and said second nucleotide sequence are hybridized to their respective portions of said polynucleotide analyte, each said sequence of nucleotides being located in its respective polynucleotide probe at or near the end thereof opposite the site of said first nucleotide sequence or said second nucleotide sequence, respectively, means for covalently attaching said first and second polynucleotide sequences when said first and second polynucleotide probes are hybridized with said polynucleotide analyte thereby forming covalently attached first and second polynucleotide sequences such that a polynucleotide primer that hybridizes to and is extended along said covalently attached sequences forms an extension product comprising said first and second polynucleotide sequences, a polynucleotide primer capable of hybridizing with said second polynucleotide probe and of being extended along said covalently attached sequences in the direction of said first polynucleotide probe, and means for extending said polynucleotide primer, said means comprising a polynucleotide polymerase and one or more deoxynucleoside triphosphates.

2. The kit of claim 1 further comprising:

a ligase as a means for covalently attaching said first and second nucleotide sequences.

3. The kit of claim 1 wherein said first polynucleotide probe has, of having, means for immobilizing said probe.

4. The kit of claim 1 wherein at least one of said first or second probe contains a polynucleotide sequence that serves as a label.

5. The kit of claim 1 wherein said first and second portions of said polynucleotide analyte are not contiguous.

* * * * *